United States Patent [19]

Manoury et al.

[11] 4,311,708
[45] Jan. 19, 1982

[54] PHENOL ETHERS

[75] Inventors: Philippe M. J. Manoury, L'Hay les Roses; Icilio A. G. Cavero; Henry Najer, both of Paris; Don P. R. L. Giudicelli, Fontenay sous Bois, all of France

[73] Assignee: Synthelabo, Paris, France

[21] Appl. No.: 20,463

[22] Filed: Mar. 14, 1979

Related U.S. Application Data

[62] Division of Ser. No. 734,359, Oct. 20, 1976, Pat. No. 4,252,984.

[30] Foreign Application Priority Data

Nov. 6, 1975 [FR] France .............................. 75 33899

[51] Int. Cl.³ .................. A01N 33/02; C07C 93/06
[52] U.S. Cl. ............................. 424/330; 260/501.17; 260/501.19; 424/316; 564/349
[58] Field of Search ............... 260/501.17, 501.15, 260/501.19, 570.7; 424/316, 330; 564/349

[56] References Cited

U.S. PATENT DOCUMENTS 3,674,840  7/1972  Grandstrom et al. ....... 260/570.7 X
3,712,890  1/1973  Lee .............................. 260/570.7 X
3,723,476  3/1973  Nakanishi et al. ........... 260/570.7 X
3,873,600  3/1978  Brandstrom et al. ........ 260/570.7 X
4,085,136  4/1978  Tucker ......................... 260/570.7 X

*Primary Examiner*—Robert V. Hines
*Attorney, Agent, or Firm*—Wegner & Bretschneider

[57] ABSTRACT

The invention provides phenol ethers of the formula:

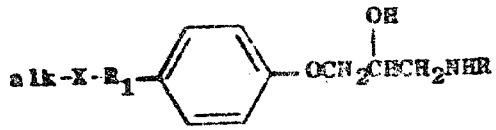

wherein
R is branched $C_{3-4}$ alkyl, $C_{3-4}$ cycloalkyl, branched cyano($C_{3-4}$ alkyl), phenyl($C_{2-3}$ alkyl), halophenyl($C_{2-3}$ alkyl), ($C_{1-4}$ alkoxy)phenyl($C_{2-4}$ alkyl), or ($C_{1-4}$ acyl)amino($C_{1-4}$ alkyl),
alk is $C_{1-4}$ alkyl substituted by a 3 to 6 membered cycloalkyl group,
X is —O—, —S— or —SO$_2$—; and
$R_1$ is —$C_{1-4}$ alkyl- or —$C_{1-4}$ alkoxy-, in their racemic and optically active forms, and their addition salts with pharmaceutically acceptable acids. These compounds are useful in therapy as β-adrenergic blocking agents. Intermediates are also provided.

18 Claims, No Drawings

PHENOL ETHERS

This is a division of application Ser. No. 734,359 filed Oct. 20, 1976, now U.S. Pat. No. 4,252,984, granted Feb. 24, 1981.

BACKGROUND OF THE INVENTION

The present invention provides a β-adrenergic blocking agent having properties which compare favorably versus the prior art "metoprolol".

SUMMARY OF THE INVENTION

In a first aspect of the invention phenol ethers are provided of the formula:

$$alk-X-R_1-\underset{}{\bigcirc}-OCH_2\overset{OH}{\underset{|}{C}}HCH_2NHR \quad (I)$$

wherein
R is branched $C_{3-4}$ alkyl, $C_{3-4}$ cycloalkyl, branched cyano($C_{3-4}$ alkyl), phenyl($C_{2-3}$ alkyl), halophenyl($C_{2-3}$ alkyl), ($C_{1-4}$ alkoxy)phenyl($C_{2-4}$ alkyl), or ($C_{1-4}$ acyl)amino($C_{1-4}$ alkyl),
alk is $C_{1-4}$ alkyl substituted by a 3 to 6 membered cycloalkyl group,
X is —O—, —S— or —SO$_2$—; and
R$_1$ is —$C_{1-4}$ alkyl- or —$C_{1-4}$ alkoxy-,
in their racemic and optically active forms, and their addition salts with pharmaceutically acceptable acids.

In a second aspect of the invention there are provided phenols of the formula:

$$alk-X-R_1-\underset{}{\bigcirc}-OH \quad (II)$$

wherein alk, X and R$_1$ are as defined above.

In a third aspect of the invention, there are provided epoxides of the formula:

$$alk-X-R_1-\underset{}{\bigcirc}-OCH_2CH\underset{O}{\overset{}{\diagdown\diagup}}CH_2 \quad (IIA)$$

wherein alk, X and R$_1$ are as defined above.

In a fourth aspect of the invention, a β-adrenergic blocking agent is provided. In one embodiment, a method is provided for administering such a β-adrenergic blocking agent, which comprises the administration to patients of a phenol ether (I) of the invention. In a second embodiment, β-adrenergic blocking agent composition is provided which comprises a pharmaceutically effective amount of a phenol ether (I) of the invention.

DETAILED DESCRIPTION OF THE INVENTION

The phenol ethers (I) of the invention may alternatively be defined in the following manner:

$$(CH_2)_pCH-(CH_2)_q-X-(CH_2)_m-(O)_n-\underset{}{\bigcirc}-OCH_2-\overset{OH}{\underset{|}{C}}H-CH_2-NHR \quad (IA)$$

in which p is an integer from 2 to 5, q is an integer from 1 to 4, m is 0, 1, 2, 3 or 4, n is 0 or 1, with the condition that if m is 0, n is also 0, X is oxygen, sulphur, or SO$_2$ and R is a branched alkyl of 3 or 4 carbon atoms, cycloalkyl of 3 or 4 carbon atoms, branched cyanoalkyl of 3 or 4 carbon atoms, phenylalkyl in which the phenyl is unsubstituted or substituted by halogen or alkoxy of 1 to 4 carbon atoms and the alkyl is branched or unbranched and has 2 to 4 carbon atoms, or acylaminoalkyl in which the acyl has 1 to 4 carbon atoms and the alkyl is branched or unbranched and has 1 to 4 carbon atoms, in their racemic and optically active forms, and their addition salts with pharmaceutically acceptable acids.

The compounds of the invention are medicaments which can be used in human and veterinary therapy, in the cardio-vascular field, as β-adrenergic blocking agents.

The phenol ethers (I) are produced by reacting a phenol (II) with a compound of the formula:

$$Z-CH_2-CH\underset{O}{\overset{}{\diagdown\diagup}}CH_2$$

wherein Z is halogen, preferably chlorine or bromine, to yield an epoxide (IIA), which is then reacted with an amine

RNH$_2$

R being as defined above, thus yielding a phenol ether (I). Alternatively, using the definition of formula (IA), the reaction scheme may be described as follows:

1. $(CH_2)_p CH-(CH_2)_q-X-(CH_2)_m-(O)_n-\underset{}{\bigcirc}-OH \quad Z-CH_2-CH\underset{O}{\overset{}{\diagdown\diagup}}CH_2 \longrightarrow$ (II')

2. $(CH_2)_p CH-(CH_2)_q-X-(CH_2)_m-(O)_n-\underset{}{\bigcirc}-O-CH_2-CH\underset{O}{\overset{}{\diagdown\diagup}}CH_2 \quad KNH_2 \longrightarrow$ (I) (IIA')

in which p, q, m, n, X and R have the same meaning as in formula (I) and Z is halogen, especially chlorine or bromine.

The phenol ethers (I) in which X is SO₂ can also be obtained by oxidising the compounds (I) in which X is S.

The condensation of the starting phenol of formula (II) (or (II')) with the epihalogenohydrin (equation 1) is advantageously carried out in an alkaline medium, at the temperature of the laboratory. The condensation with the primary amine (equation 2) may be carried out at the same temperature, most frequently in the absence of any solvent.

The phenols II are new and can be obtained by various processes, depending on the meanings of n and m; these processes are described in detail in the Examples. In general terms they are as follows:

For the compounds in which X is 0 or S and n is 1, the starting material is, for example, either p-benzoxyphenol of the formula

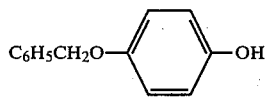

or hydroquinone, which is reacted with a compound of the formula

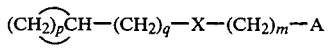

in which p, q, X and m have the meanings given above and A is chlorine or a mesylate or tosylate group. Thereafter, if the compound of formula III is used as the starting material, debenzylation is carried out by hydrogenation, preferably at ambient temperature, in an alcohol of low molecular weight, in the presence of a catalyst.

For the compounds where X is 0 and n is 0, the starting material is, for example, the compound of the formula:

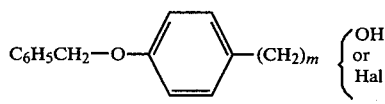

which is reacted with a compound of the formula:

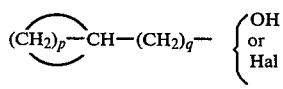

after which debenzylation is carried out as before.

For the compounds for which X is 0 and m and n are both equal to 0, the compound of formula III is reacted with a compound of the formula:

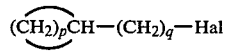

after which debenzylation is carried out as before.

In the preceding formulae V to VII, p, q and X have the meanings indicated above.

The Examples which follow illustrate the invention, M.p.=melting point and temperatures are in °C.

EXAMPLE I

1-{4-[2-Cyclopropylmethoxy)-ethoxy]-phenoxy}-3-isopropylamino-propan-2-ol and its hydrochloride

[(I); m=2; n=1; p=2; q=1; R=—CH—(CH₃)₂; X=0; code number: SL-D.177]

Preparation of the starting compound II 0.1 mol of sodium methylate is prepared in a 250 ml 3-necked flask equipped with a magnetic stirrer, a reflux condenser and a dropping funnel. 20.02 g (0.1 mol) of p-benzoxyphenol (Schühardt, Munich) and 19.4 g (0.1 mol) of 2-cyclopropylmethoxy-ethyl mesylate are then added. The mixture is kept at a reflux temperature for 4 hours, the precipitate which has formed is filtered off and the solution is evaporated to dryness. The residue from the evaporation is taken up in ether, the organic phase is washed with an 0.05 N sodium hydroxide solution and then with water, dried over sodium sulphate, filtered and evaporated to dryness, and the residue is distilled under reduced pressure. 18.5 g (yield: 63%) of 1-benzoxy-4-[2-(cyclopropylmethoxy)-ethoxy]-benzene, which boils at 180°–185° C./0.05 mm Hg and crystallises (M.p. <50° C.) are thus obtained.

45 g of the above compound, dissolved in 20 ml of methanol, are debenzylated by hydrogenation over palladium-on-charcoal under 50 kg pressure at ambient temperature. The catalyst is filtered off, the solvent is evaporated, and 30.8 g of 4-[2-(cyclopropylmethoxy)ethoxy]-phenol (yield=99%), sufficiently pure for continuing the synthesis, are obtained.

(1) A suspension of 31.8 g (0.152 mol) of 4-[2-(cyclopropylmethoxy)-ethoxy]-phenol in 550 ml of water is introduced into a 1 liter Erlenmeyer flask equipped with a magnetic stirrer, a dropping funnel and a reflux condenser. 7.6 g of sodium hydroxide pellets are then added whilst keeping the temperature below 20° C.; thereafter 21.02 g (0.228 mol) of epichlorohydrin are introduced dropwise. The reaction mixture is kept at ambient temperature for 8 hours. The organic phase is decanted, the aqueous phase is washed with ether and the ether extract is combined with the original organic solution. The whole is washed with a 2 N sodium hydroxide solution and then with water, and dried over sodium sulphate, and the ether is distilled.

37 g (yield=92.5%) of 1-{4-[2-(cyclopropylmethoxy)-ethoxy]-phenoxy}-2,3-epoxy-propane are thus obtained, and this material is used directly in the next stage.

(2) 4 g of the preceding compound are reacted with 10 ml of isopropylamine in a 50 ml Erlenmeyer flask at ambient temperature for 72 hours. The mixture is evaporated to dryness, the residue is taken up in toluene and the solvent is evaporated. 3.7 g of 1-{4-[2-(cyclopropylmethoxy)-ethoxy]-phenoxy}-3-isopropylamino-propan-2-ol (yield=77%) are obtained. The crude compound is converted directly to its hydrochloride. *Hydrochloride of the compound* (SL-D.177). The preceding base is dissolved in the minimum amount of ethanol, the solution is acidified with a solution of hydrogen chloride gas in ether, and ether is added until the mixture turns cloudy. The hydrochloride which has precipitated is filtered off and recrystallised from a mixture of ethanol and ether.

2.7 g of the hydrochloride, which melts at 94°–96° C. (yield=66%) are thus obtained.

Analysis: Calculated %: C 60.07; H 8.40; N 3.89; Cl 9.85. Found %: C 59.88; H 8.51; N 4.03; Cl 9.80; C 59.92; H 8.59; N 3.90; Cl -.

The NMR spectrum is in agreement with the structure.

EXAMPLE II

1-{4-[2-(Cyclopropylmethoxy)-ethoxy]-phenoxy}-3-t-butylamino-propan-2-ol and its neutral fumarate

[(I): m=2; n=1; p=2; q=1; X=0; R=—C—(CH$_3$)$_3$; code number: SL-D.178]

Following the procedure of Example I, 1-{4-[2-(cyclopropylmethoxy)-ethoxy]-phenoxy}-2,3-epoxy-propane is prepared and then treated with t-butylamine. 7.6 g (yield=74%) of crude 1-{4-[2-(cyclopropylmethoxy)-ethoxy]phenoxy}-3-t-butylamino-propan-2-ol are thus obtained, and this material is converted to the fumarate by mixing stoichiometric amounts of the base and of the acid in solution in isopropanol. The neutral fumarate which has precipitated is filtered off and recrystallised from ethanol (yield=80%), M.p.=158°-160° C.

Analysis: Calculated %: C 63.77; H 8.41; N 3.54. Found %: C 63.61; H 8.63; N 3.58; C 63.60; H 8.76; N 3.53.

The NMR spectrum has confirmed the structure of the compound.

EXAMPLE III

1-{4-[2-(Cyclopropylmethoxy)-ethyl]-phenoxy}-3-isopropylamino-propan-2-ol and its hydrochloride

[(I): m=2; n=0; p=2; q=1; R=CH—(CH$_3$)$_2$; X=0; code number: SL-D.212]

Preparation of the starting compound 78.5 g (0.435 mol) of ethyl p-hydroxyphenylacetate, partially dissolved in 100 ml of ethanol, are introduced into a one liter 3-necked flask equipped with a mechanical stirrer, a dropping funnel, a reflux condenser and a thermometer and a solution of sodium ethylate (prepared from 100 ml of ethanol and 10.01 g of sodium), followed by 55 ml (0.4785 mol) of pure benzyl chloride are added dropwise. The mixture is kept at the reflux temperature of the solvent for 8 hours, the sodium chloride precipitated is then filtered off and the solution is evaporated to dryness. The residue is dissolved in ether and the ether solution is washed first with water, then with a N sodium hydroxide solution and again with water. It is dried over sodium sulphate, the ether is evaporated and the residue is rectified.

80.2 g (yield=68%) of ethyl p-benzoxyphenylacetate boiling at 180°/0.07 mm Hg, are thus obtained.

200 ml of tetrahydrofurane are introduced into a 2 liter reactor equipped with a mechanical stirrer, a dropping funnel, a reflux condenser and a thermometer and are cooled before adding 6.6 g of lithium aluminium hydride under a nitrogen atmosphere. This suspension is cooled to −5° and 80 g (0.296 mol) of ethyl p-benzoxyacetate are added dropwise thereto in such a way that the temperature does not exceed 0°.

The whole is then kept at ambient temperature for 3 hours. The reaction mixture is then cooled and the excess AlLiH$_4$ is destroyed with an excess of sodium potassium double tartrate, the mixture is filtered and the residue is evaporated.

The 2-(p-benzoxyphenyl)-ethanol is caused to crystallise by trituration in isopropyl ether. 58.4 g (yield=86%) of this product are obtained; M.p.: 86°-88°.

2.6 g (0.055 mol) of sodium hydride are suspended in 20 ml of dimethylformamide in a 250 ml flask equipped with a magnetic stirrer, a dropping funnel and a reflux condenser. 11.4 g (0.05 mol) of 2-(p-benzoxyphenyl)-ethanol dissolved in 30 ml of the same solvent are then added. The mixture is gently heated to 30° and a further 70 ml of dimethylformamide are then added. A precipitate is observed. 7.42 g (0.055 mol) of cyclopropylmethyl bromide dissolved in 20 ml of dimethylformamide are then added and the mixture is heated for 8 hours to a temperature of 60°.

Progressive disappearance of the solid product is observed.

The reaction mixture is poured into water and extracted with ether, and the ether solution is washed with water, dried over sodium sulphate and evaporated to dryness. The solid residue is stirred for 30 minutes in petroleum ether; the insoluble 2-(p-benzoxyphenyl)-ethanol which has not reacted is then filtered off, the solvent is evaporated and the residue is rectified.

5.9 g (yield=74%) of 4-[2-(cyclopropylmethoxy)-ethyl]-1-benzoxy-benzene are thus obtained. Boiling point=182°-184°/0.07 mm Hg.

The debenzylation of the preceding compound to 4-[2-(cyclopropylmethoxy)-ethyl]-phenol is carried out under conditions similar to those described in Example I. The phenol is obtained in a yield of 84%. It boils at 138°/0.07 mm Hg.

(1) 1 g of sodium hydroxide pellets (0.025 mol) is added to a suspension of 3.8 g of the preceding compound in 30 ml of water. When the solution is homogeneous, 2.3 ml of epichlorohydrin are added and the mixture is stirred for 8 hours. It is then extracted with ether and the extract is washed with water, dried over sodium sulphate and evaporated to dryness.

The compound is purified by passing it over a silica column. 2.4 g of 1-{4-[2-(cyclopropylmethoxy)ethyl]-phenoxy}-2,3-epoxy-propane are thus obtained (Rf=0.45; SiO$_2$; CHCl$_3$).

(2) 4.9 g of the preceding compound (0.02 mol) are condensed with 25 ml of isopropylamine by contact for 8 hours at ambient temperature and then by heating for 48 hours at the reflux temperature. After evaporation to dryness, the compound obtained is crystallised from petroleum ether.

5 g (yield=80%) of 2-{[4-(2-cyclopropylmethoxy)-ethyl]-phenoxy}-3-isopropylamino-propan-2-ol are thus obtained. M.p.=70°-72° C.

Hydrochloride (SLD-212).

This is prepared by dissolving the base in the minimum amount of acetone and adding a solution of hydrochloric acid in ether until the pH is acid. The hydrochloride which has precipitated is filtered off and is recrystallized twice from acetone. M.p.=116° C.

Analysis: Calculated %: C 62.86; H 8.79; N 4.07; Cl 10.30. Found %: C 62.48; H 8.74; N 4.07; Cl 10.50; C 62.56; H 8.65; N 3.98; Cl 10.54.

The NMR spectrum has confirmed the structure.

EXAMPLE IV

1-[4-(Cyclopropylmethoxymethyl)-phenoxy]-3-isopropylamino-propan-2-ol

[(I); m=1; n=0; p=2; q=1; R=—CH—(CH$_3$)$_2$; X=0; code number: SL-D.224]

Preparation of the starting compound.

p-Benzoxybenzyl chloride is prepared in accordance with the method of Shelton and Van Campar (J. Am. Chem. Soc. 1953, 75, 5,491–5,495). It melts at 78°.

To a suspension of 1.07 g of 50% strength sodium hydride in 10 ml of dimethylformamide is added dropwise a solution of 1.5 g of cyclopropylmethanol dissolved in 10 ml of the same solvent, followed by 5.5 g of p-benzoxybenzyl chloride dissolved in 20 ml of dimethylformamide. The reaction mixture is left standing overnight; it is then poured into water, the aqueous phase is extracted with ether, the extract is washed with water and dried over sodium sulphate, and the solvent is evaporated.

The residue oil (boiling point: 190°/0.1 mm) is finally distilled. 4.5 g (yield=75%) of 1-benzoxy-4-(cyclopropylmethoxymethyl)-benzene are thus obtained.

The preceding compound is debenzylated in the usual manner and the 4-(cyclopropylmethoxymethyl)-phenol thus obtained is purified by a pass over silica (RF=0.1; $SiO_2$; $CHCl_3$). 1 & 2) The preceding phenol is condensed with epichlorohydrin. The intermediate obtained is reacted with isopropylamine under conditions similar to those described in the preceding examples.

1-[4-(cyclopropylmethoxymethyl)-phenoxy]-3-isopropylamino-propan-2-ol is obtained in a yield of 50%. The compound melts at 48°. The structure is confirmed by NMR spectroscopy.

Analysis: Calculated %: C 69.59; H 9.27; N 4.77. Found %: C 69.65; H 9.57; N 4.72; C 69.52; H 9.34; N 4.70.

EXAMPLE V

1-[4-(Cyclopropylmethoxy)-phenoxy]-3-isopropylamino-propan-2-ol and its hydrochloride

[(I); m=0; n=0; p=2; q=1; R=—CH(CH$_3$)$_2$; X=0; code number: SL-D.230]

Preparation of the starting compound.

40 g of p-benzoxyphenol are suspended in 100 ml of methanol. A solution of sodium methylate (200 ml of methanol and 4.6 g of Na) is added, after which 29 g (0.22 mol) of cyclopropylmethyl bromide are added dropwise. The reaction mixture is kept at the reflux temperature for 8 hours, the precipitate obtained is filtered off and dissolved in chloroform, the chloroform solution is washed with water and dried over sodium sulphate, and the solvent is evaporated.

25 g (yield=50%) of 4-(cyclopropylmethoxy)-1-benzoxy-benzene are thus obtained. M.p.=96°.

This ether is dibenzylated in the usual manner. The 4-(cyclopropylmethoxy)-phenol is crystallised from petroleum ether (yield=86%). M.p. <50°.

(1) 13 g (0.08 mol) of 4-(cyclopropylmethoxy)-phenol are suspended in 150 ml of water in a 500 ml Erlenmeyer flask. 4 g of sodium hydroxide pellets are added, and it is found that the phenol dissolves. 16.4 g (0.12 mol) of epibromohydrin are then introduced dropwise. The mixture is stirred for 8 hours at ambient temperature. The reaction mixture is then taken up in ether and the ether phase is washed with water, then with 0.05 N sodium hydroxide and again with water, dried over sodium sulphate and evaporated to dryness.

14 g (yield=79%) of 1-[4-(cyclopropylmethoxy)-phenoxy]-2,3-epoxy-propane, melting at 56° after recrystallisation from petroleum ether, are obtained.

(2) The preceding compound is condensed with isopropylamine under conditions similar to those described above. 1-[4-(cyclopropylmethoxy)-phenoxy]-3-isopropylamino-propan-2-ol is obtained in a yield of 60%.

After recrystallisation from petroleum ether and then from hexane, the compound melts at 78°–80°.

The preceding base is converted to its hydrochloride by dissolving it in isopropanol and adding a solution of hydrogen chloride gas in ether (yield=60%). M.p.=143°–144°.

Analysis: Calculated %: C 60.84; H 8.29; N 4.43; Cl 11.22. Found %: C 60.94; H 8.12; N 4.28; Cl 11.22; C 60.78; H 8.33; N 4.25; Cl 11.42.

The NMR spectrum has confirmed the structure of the compound.

EXAMPLE VI

1-[4-(Cyclopropylmethoxy)-phenoxy]-3-t-butyl amino-propan-2-ol and its hydrochloride

[(I); m=0; n=0; p=2; q=1; R=—C(CH$_3$)$_3$; X=0; code number: SL-D.231]

The procedure followed is as in Example V, but the isopropylamine is replaced by t-butylamine.

1-[4-(Cyclopropylmethoxy)-phenoxy]-3-t-butylamino-propan-2-ol is obtained in a yield of 50% and melts at 90°–92°.

Its hydrochloride (yield=55%) melts at 146°–147°.

Analysis: Calculated %: C 61.89; H 8.55; N 4.24; Cl 10.74. Found %: C 61.79; H 8.71; N 4.04; Cl 10.72; C 61.75; H 8.71; N 4.08; Cl 10.95.

The NMR spectrum has confirmed the structure of the compound.

EXAMPLE VII

1-{4-[2-(Cyclobutylmethoxy)-ethyl]-phenoxy}-3-isopropylamino-propan-2-ol

[(I); m=2; n=0; p=3; q=1; R=—CH—(CH$_3$)$_2$; X=0; code number: SL-D.254]

Preparation of the starting compound.

12.7 ml (0.167 mol) of methanesulphonyl chloride are added dropwise to a solution, cooled to −20°, of 32.2 ml of triethylamine (0.23 mol) and 12.7 g (0.15 mol) of cyclobutylcarbinol, in such a way that the temperature does not exceed −10°. The reaction mixture is then left at ambient temperature for half an hour, 500 ml of ether are added, the triethylamine hydrochloride is filtered off, the ether phase is washed successively with 100 ml of N hydrochloric acid, 100 ml of 5 N sodium hydroxide and then with water and is dried over sodium sulphate, the solution is filtered, the solvent is evaporated and the residual oil is distilled under reduced pressure.

11 g of cyclobutylmethyl mesylate, boiling at 96°/0.1 mm Hg, are thus obtained.

10 g of 2-(p-benzoxyphenol)-ethanol are converted to the sodium derivative with 2.2 g of 50% strength sodium hydride in dimethylformamide, with gentle heating to assist the reaction. 7.7 g (0.047 mol) of cyclobutylmethyl mesylate in 10 ml of the same solvent are then added. The reaction mixture is heated to 60°–70° for 18 hours and is poured into water and extracted with ether, and the extract is washed with water, dried over sodium sulphate and evaporated to dryness. The residual oil is taken up in petroleum ether, and insoluble material (2.3 g of the starting alcohol, which has not reacted) is filtered off, the solvent is evaporated and the residual oil is then distilled under reduced pressure.

8 g (yield = 80%) of 4-[2-(cyclobutylmethoxy)-ethyl]-1-benzoxy-benzene are thus obtained. Boiling point = 115°/0.01 mm of mercury.

The debenzylation of the preceding compound to give 4-[2-(cyclobutylmethoxy)-ethyl]-phenol

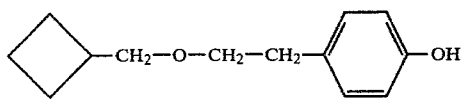

is carried out under conditions similar to those described in the preceding Examples. This phenol is obtained in a yield of 82%.

(1) The preceding phenol is treated with epibromohydrin under conditions similar to those described in Example III and 1-{4-[2-(cyclobutylmethoxy)-ethyl]-phenoxy}-2,3-epoxy-propane is isolated in good yield and is used, without further purification, for the continuation of the synthesis.

(2) 5.4 g (0.02 mol) of the preceding compound are reacted with 25 ml of isopropylamine for 36 hours at the reflux temperature. The mixture is evaporated to dryness, the residual oil is taken up in toluene, and the solution is again evaporated. The evaporation residue is taken up in dilute hydrochloric acid and ether, and the acid aqueous phase is extracted with ether, rendered alkaline by means of sodium bicarbonate and finally extracted a last time with ether. The ether phase is dried over sodium sulphate and filtered, the solvent is evaporated and a residual oil is obtained, which crystallises from pentane and which is recrystallised from hexane.

2 g (yield = 33%) of 1-{4-[2-cyclobutylmethoxy)-ethyl]-phenoxy}-3-isopropylamino-propan-2-ol, melting at 62°–63°, are thus obtained.

Analysis: Calculated %: C 70.99; H 9.72; N 4.35. Found %: C 70.88; H 9.90; N 4.29; C 71.06; H 9.84; N 4.21.

The NMR spectrum confirms the structure of the compound.

The hydrochloride (SLE-020) of this compound melts at 104° C.

The acid fumarate melts at 157° C.

EXAMPLE VIII

1-{4-[2-(Cyclohexylmethoxy)-ethyl]-phenoxy}-3-isopropylamino-propan-2-ol and its hydrochloride

[(I); m=2; n=0; p=5; q=1; R=—CH—(CH$_3$)$_2$; X=0; code number: SL-D.268]

The following are prepared successively in a similar manner to that which has been described in Example VII: cyclohexylmethyl mesylate; M.p. 50°, 
4-[2-(cyclohexylmethoxy)-ethyl]-1-benzoxy-benzene; boiling point 170°/0.06 mm, 
4-[2-(cyclohexylmethoxy)-ethyl]-phenol, which is an oil which was not purified, 
1-{4-[2-(cyclohexylmethoxy)-ethyl]-phenoxy}-2,3-epoxypropane, an oil which is used, without redistillation, for the continuation of the synthesis, 
1-{4-[2-cyclohexylmethoxy)-ethyl]-phenoxy}-3-isopropylamino-propan-2-ol, which is immediately converted to its hydrochloride. The latter melts at 122°.

Analysis: Calculated %: C 65.34; H 9.39; N 3.62; Cl 9.18. Found %: C 65.31; H 9.58; N 3.63; Cl 8.98; C 65.49; H 9.72; N 3.78; Cl 9.17.

The NMR spectrum has confirmed the structure of this compound.

EXAMPLE IX 1-(4-Cyclopropylpropoxy-phenoxy)-3-isopropylamino-propan-2-ol and its hydrochloride

[(I); p=2; q=3; m=0; n=0; R=CH(CH$_3$)$_2$; X=0; code number: SL-D.311]

Preparation of the starting compound: 4-cyclopropylpropoxy-phenol.

7.8 g of cyclopropylpropanol dissolved in 16.7 ml of triethylamine are cooled to between −20° C. and −30° C. Thereafter, 6.6 ml of methanesulphonyl chloride are added, with vigorous stirring, in such a way that the temperature does not exceed −10° C.

The reaction mixture is found to set solid shortly before the end of the addition. 200 ml of ether are added and the mixture is filtered. The ether phase is washed with 3 N hydrochloric acid and then with a NaHCO$_3$ solution. After drying, and evaporating the ether, 12.4 g (yield: 90%) of cyclopropylpropyl mesylate are obtained in the form of an oil.

12.43 ml of a 5.6 N mixture of sodium methylate and methyl alcohol (1 equivalent) are added to 13.9 g of p-benzoxyphenol in 60 ml of ethanol. Thereafter, 12.4 g of cyclopropylpropyl mesylate in 40 ml of ethanol are introduced, all at once, and the mixture is heated to the reflux temperature of this solvent for 3 hours. The ethanol is driven off by distillation, the residue is taken up in chloroform and the solution is washed with water, with N sodium hydroxide solution and then with water. From the chloroform (solution) are obtained 15.4 g of 4-cyclopropyl-propoxy-1-benzoxy-benzene (yield: 78.5%), M.p. = 60° C. (MeOH).

14.6 g of 4-cyclopropylpropoxy-1-benzoxybenzene suspended in 500 ml of methanol are subjected to catalytic hydrogenation (catalyst: 10% strength Pd/C; temperature: 20° C.; atmospheric pressure).

After filtration, and evaporation of the methanol, 9 g of 4-cyclopropylpropoxy-phenol are obtained (yield: 90.5%). M.p. = 37° C. (Tottoli).

(1) A mixture of 9 g of 4-cyclopropylpropoxy-phenol, 150 ml of water, 3 g of KOH and 7.7 g of epibromohydrin is stirred for 15 hours at ambient temperature. The reaction mixture is extracted with ether and the extract is washed with N NaOH and then with water. The ether is evaporated and the excess epibromohydrin is removed by entrainment with xylene (distillation at 15 mm Hg). 1-(4-Cyclopropylpropoxy-phenoxy)-2,3-epoxy-propane is obtained in a yield of 100%.

(2) 11.7 g of crude 1-(4-cyclopropylpropoxy-phenoxy)-2,3-epoxy-propane dissolved in 50 ml of isopropylamine are left to stand for 30 hours. After refluxing for 3 hours to complete the reaction, the excess isopropylamine is evaporated and the residue is taken up in ether, to which one equivalent of a solution of hydrogen chloride in ether is added.

10 g of the crude hydrochloride of 1-(4-cyclopropyl-propoxy-phenoxy)-3-isopropylamino-propan-2-ol are thus obtained and are recrystallised twice from a 90/10 mixture of isopropyl ether and isopropanol (weight obtained = 8.45 g). Yield: 53% (relative to the phenol). M.p. = 115° C.

Analysis: Calculated %: C 62.87; H 8.79; O 13.96; N 4.07; Cl 10.31. Found %: C 62.83; H 9.15; O 14.30; N 3.98; Cl 10.28.

H$_2$O = 0.2%

EXAMPLE X 4-(2-cyclobutylmethoxy-ethoxy)-1-phenoxy-3-isopropylamino-propan-2-ol and its hydrochloride

[(I); p=3; q=1; m=2; n=1; R=CH(CH$_3$)$_2$; X=0 code number: SL-E 096]

Preparation of the starting compound: 2-cyclobutylmethoxy-4-ethoxy-phenol.

246.8 g of cyclobutyl-methanol, 42 g of ethylene oxide and 2.8 g of sodium are introduced very rapidly into a 250 ml stainless steel bomb cooled to −15° C. The bomb is closed and is allowed to return to ambient temperature. It is then heated at 60° C. for 4 hours. The excess cyclobutyl-methanol is then distilled under atmospheric pressure and subsequently under a water pump vacuum. 52 g (yield: 40%) of cyclobutyl-methoxyethanol are obtained.

32 ml of pyridine are cooled to −10° C. in a 100 ml Erlenmeyer flask equipped with a thermometer and a magnetic stirrer, and 19.3 g of p-toluenesulphonyl chloride are then added all at once. 13 g of the preceding alcohol, dissolved in 16.4 ml of pyridine are then added dropwise without exceeding 0° C. The reaction is very exothermic. The mixture is allowed to return to ambient temperature and is left to stand overnight. It is poured onto ice, acidified with 70 ml of concentrated hydrochloric acid and extracted three times with ether, and the extract is washed with water, with sodium bicarbonate solution and then with water, dried over MgSO$_4$, filtered and evaporated to dryness. 21 g of an oil are isolated and purified by chromatography. 17.4 g (yield: 70%) of the tosylate of 1-cyclobutylmethoxyethanol are thus isolated.

1.58 g of sodium in 48.3 ml of methanol are introduced into a 250 ml three-neck flask equipped with a magnetic stirrer, a thermometer and a condenser, and 13.8 g of p-benzoxyphenol are then added all at once. The mixture is stirred for 30 minutes, after which solution is complete (deep chestnut colour). 17.4 g of the preceding tosylate are now introduced and the mixture is heated under reflux for 4 hours. The inorganic salts are filtered off hot, the filtrate is evaporated to dryness, the residue is taken up in ether and the organic phase is washed with 5 N sodium hydroxide solution and then with water, dried over Na$_2$SO$_4$ and evaporated to dryness. 11.5 g (yield: 60%) of the benzyl ether of 4-2(-cyclobutylmethoxyethoxy)-phenol are isolated in the form of an oil.

25.2 g of the preceding product, dissolved in 150 ml of methanol, are hydrogenated with 2.5 g of 10% strength palladium/C under a pressure of 40 kg/cm$^2$, at 40° C.

The catalyst is filtered and the filtrate is evaporated to dryness. 16.7 g of 4-(2-cyclobutylmethoxyethoxy)-phenol are isolated and used in the crude form in the next stage.

(1) 16.7 g of the preceding phenol and 75 ml of normal sodium hydroxide solution are introduced into a 250 ml Erlenmeyer flask equipped with a magnetic stirrer, a thermometer and a condenser. The mixture is stirred for 15 minutes; complete solution is observed. 20.6 g of epibromohydrin are then added. The mixture is stirred for 10 hours at ambient temperature and extracted with ether. The extract is washed with water, 2 N sodium hydroxide solution and then with water, dried over MgSO$_4$, filtered and evaporated to dryness.

20.5 g (yield: 98%) of 4-(2-cyclobutylmethoxyethoxy)-phenoxy-2,3-epoxy-propane are isolated in the form of an oil.

(2) The preceding epoxide, and 70 ml of isopropylamine, are placed in a 250 ml Erlenmeyer flask equipped with a stirrer. The mixture is heated under reflux for 5 hours. The reaction is complete.

The mixture is evaporated to dryness. The residue is dissolved in an acid medium and reconverted to the base, which is extracted with ether. The extract is washed with water, dried over MgSO$_4$, filtered and evaporated to dryness. The residual oil crystallises from petroleum ether; all the impurities are removed.

The product is recrystallised from hot petroleum ether. 10 g (yield: 40%) of 1-[4-(2-cyclobutylmethoxyethoxy)-phenoxy]-3-isopropylamino-propan-2-ol are obtained. M.p.=56° C.

Hydrochloride (SLE-096).

The base is dissolved in a minimum amount of isopropanol, a solution of hydrogen chloride in ether is added, and the hydrochloride is then rendered insoluble by adding ether until the mixture turns slightly cloudy. The hydrochloride crystallises slowly.

After recrystallisation, 7 g of pure hydrochloride are isolated. M.p.=97° C.

Analysis: Calculated %: C 61.03; H 8.62; O 17.11; N 3.75; Cl 9.48. Found %: C 60.89; H 8.45; O 17.35; N 3.79; Cl 9.41; C 61.14; H 8.79 ; N 3.73.

EXAMPLE XI

1-[4-(2-Cyclobutylmethoxy-ethyl)-phenoxy]-3-(1-methyl-2-cyano-ethylamino)-propan-2-ol and its hydrochloride

[(I); p = 3; q = 1; m = 2; n = 0; R = $-\underset{\underset{CH_3}{|}}{CH}-CH_2-CN$; X = 0 code number: SLE.024]

8 g of 1-[4-(2-cyclobutylmethoxy-ethyl)-phenoxy]-2,3-epoxy-propane, prepared in Example VII, and 10.13 g of 1-methyl-2-cyano-ethylamine are introduced into a 100 ml Erlenmeyer flask equipped with a magnetic stirrer and an air-cooled condenser. The mixture is stirred at ambient temperature for 5 hours and is then left to stand overnight.

The excess amine is evaporated under a water pump vacuum.

The residual oil is purified by washing with an acid medium.

5.15 g (yield: 50%) of 1-[4-(2-cyclobutylmethoxyethyl)-phenoxy]-3-(1-methyl-2-cyano-ethylamino)-propan-2-ol are isolated in the form of a pale yellow oil. The oil is dissolved in 20 ml of isopropyl alcohol and 1 cm$^3$ of concentrated HCl is then added. The hydrochloride is rendered insoluble by adding ether until the mixture turns slightly cloudy. The hydrochloride crystallises slowly.

After recrystallisation from a mixture of isopropanol and ether, 4.2 g of hydrochloride are isolated. M.p.=126° C. Yield=40%.

Analysis: Calculated %: C 62.73; H 8.16; N 7.31; Cl 9.26. Found %: C 62.31; H 8.28; N 7.26; Cl 9.28; C 62.33; H 8.14; N 7.28; Cl 9.13.

EXAMPLE XII

1-[4-(2-Cyclobutylmethoxy-ethyl)-phenoxy]-3-(2-acetylamino-ethylamino)-propan-2-ol and its hydrochloride.

[(I); p=3; q=1; m=2; n=0; R=CH$_3$CONHCH$_2$CH$_2$; X=O; code number: SL-E.025]

8 g of 1-[4-(2-cyclobutylmethoxy-ethyl)-phenoxy]-2,3-epoxy-propane prepared in Example VII and 12.4 g of N-acetyl-ethylenediamine are introduced into a 100 ml Erlenmeyer flask equipped with a magnetic stirrer.

The mixture is stirred at ambient temperature for 5 hours and is then left to stand overnight.

It is poured onto water, and the product is filtered off and washed twice more with water. After having been dried, 8.3 g (yield: 75%) of 1-[4-(2-cyclobutylmethoxy-ethyl)-phenoxy]-3-(2-acetylamino-ethylamino)propan-2-ol are isolated. M.p.=108° C.

Hydrochloride (SLE-025).

The hydrochloride is prepared by dissolving the base in a minimum amount of ethyl alcohol and 1.5 cm$^3$ of concentrated HCl are then added dropwise. The hydrochloride is rendered insoluble by adding ether until the mixture turns slightly cloudy and is then left to crystallise.

After recrystallisation from a mixture of ethanol and ether, 4.8 g (yield: 40%) of hydrochloride are isolated. M.p.=150° C.

Analysis: Calculated %: C 59.61; H 8.75; N 6.95; Cl 8.79. Found %: C 59.38; H 8.58; N 6.85; Cl 8.92. C 59.60; H 8.63; N 6.87.

EXAMPLE XIII

1-[4-(2-Cyclopropylmethylthio-ethoxy)-phenoxy]-3-isopropylamino-propan-2-ol and its hydrochloride

[(I); p=2; q=1; m=2; n=1; R=CH(CH$_3$)$_2$; X=S; code number: SLD-299]

Preparation of the starting compound:
4-(2-cyclopropylmethylthio-ethoxy)-phenol.

4.4 g (0.04 mol) of hydroquinone are dissolved in 10 cm$^3$ of DMF and 1.78 cm$^3$ (0.01 mol) of 5.8 N MeONa are added under nitrogen. The sodium derivative precipitates.

The suspension is heated to about 60° C. and 1.5 g (0.01 mol) of cyclopropyl-methylthio-ethyl chloride in 10 cm$^3$ of DMF are added very slowly. The addition is carried out over the course of half an hour. The mixture is heated at 70° C. for three hours, the DMF is driven off on an evaporator and the residue is taken up in chloroform. A part of the hydroquinone precipitates. It is filtered off.

The chloroform solution is washed twice with water and then dried over MgSO$_4$ and concentrated.

After passing over a silica column in CH$_2$Cl$_2$, the desired product is obtained at the top. 1.1 g of pure product are obtained. Yield: 50%.

(1) 6.7 g of the preceding phenol are dissolved in 29.9 cm$^3$ of N NaOH. 4.8 g (20% excess) or 3 cm$^3$ of epibromohydrin are added. The mixture is stirred for 1 hour at ordinary temperature. A further 1.5 cm$^3$ are added. The mixture is stirred for a further 2 hours and is extracted twice with ether. The ether solutions are washed with water, dried and concentrated.

Toluene is added and the mixture is heated at 60° C. to remove the excess epibromohydrin. 7.8 g (yield: 94%) of 1-[4-(2-cyclopropylmethylthio-ethoxy)-phenoxy]-2,3-epoxy-propane are obtained.

(2) 7.8 g of the preceding epoxide are reacted with 50 cm$^3$ of isopropylamine and 2 drops of water. The mixture is left overnight at ordinary temperature.

It is then concentrated on an evaporator.

The residue is dissolved in CH$_2$Cl$_2$ and is passed over a silica column (10 g per gram of product).

The product is only eluted by methanol.

1-[4-(2-Cyclopropylmethylthio-ethoxy)-phenoxy]-3-isopropylamino-propan-2-ol crystallises (2.5 g). M.p.= <45° C. Yield 27%.

Hydrochloride (SLD-299): M.p.=86° C.

EXAMPLE XIV

1-[4-(2-Cyclobutylmethylthio-ethyl)-phenoxy]-3-isopropylamino-propan-2-ol and its hydrochloride

[(I): p=3; q=1; m=2; n=0; R=CH(CH$_3$)$_2$; X=S; code number: SLE-056]

Preparation of the starting compound:
4-(2-Cyclobutylmethylthio-ethyl)-phenol.

A solution of 100 g (0.60 mol) of p-methoxyphenylacetic acid in ether is introduced into a 4 l reactor, under nitrogen, which contains 28 g (0.74 mol) of lithium aluminum hydride and 600 ml of anhydrous ether. The mixture is heated under reflux for 3 hours and then cooled in a bath of ice and salt and the excess hydride is removed by cautiously adding 25 ml of water, followed by 25 ml of 15% strength NaOH and, finally, 20 ml of water. The white precipitate is removed by filtration, and after evaporation of the ether, 80 g of an oil are obtained. This oil, when distilled under 0.07 mm Hg at a temperature of 115° C., gives 77 g of 2-(p-methoxyphenyl)-ethan-1-ol. Yield: 85%.

7 g (0.026 mol) of phosphorus tribromide are cooled in a bath of ice and salt. At the same temperature, 2 g (0.013 mol) of 2-(p-methoxyphenyl)-ethan-1-ol are added fairly rapidly. The mixture is allowed to return to ambient temperature, whilst stirring, and is then heated under reflux for about 2 hours. The excess phosphorus tribromide is evaporated. The residue is cooled by means of ice and salt, water is added cautiously, and the oil is extracted with ether. The ether phase is washed repeatedly with water and dried over magnesium sulphate. After evaporating the ether, 2.4 g of oil are obtained. This oil is distilled under 10 mm Hg at a temperature of 140° C. and 2.4 g of 2-(p-methoxyphenyl)-ethyl are obtained. Yield: 85%.

Analysis: Calculated %: C 50.26; H 5.15; Br 37.15. Found %: C 50.54; H 5.14; Br 37.17; C 50.56; H 5.29; Br 37.11.

28 g (0.130 mol) of 2-(p-methoxyphenyl)-ethyl bromide, 9.90 g (0.130 mol) of thiourea and 250 ml of ethanol are introduced into an Erlenmeyer flask placed under nitrogen and equipped with a stirrer and a reflux condenser. The mixture is heated under reflux for about 2 hours. It is then allowed to cool and 130 ml of 2 N sodium hydroxide solution are added. This mixture is heated under reflux for 2 hours. The ethanol is evaporated and after cooling the residue is acidified with concentrated hydrochloric acid and extracted with ether. The ether phase is washed with water, with an aqueous bicarbonate solution and again with water and is dried over magnesium sulphate, and the ether is evaporated. 21.4 g of oil are obtained; this oil, after distillation under 0.1 mm Hg at a temperature of 115° C., gives 19.2 g of 2-(p-methoxyphenyl)-ethanethiol. Yield: 88%.

Analysis: Calculated %: C 64.25; H 7.19; S 19.06. Found %: C 64.55; H 7.43; S 18.96; C 64.33; H 7.40; S 19.05.

11 g (0.065 mol) of 2-(p-methoxyphenyl)-ethanethiol and 4.23 g (0.065 mol) of potassium hydroxide pellets dissolved in 70 ml of methanol are introduced into an Erlenmeyer flask which is equipped with a magnetic stirrer and a reflux condenser and is placed under nitrogen. The mixture is stirred at ambient temperature and 11.16 g (0.068 mol) of cyclobutylmethyl mesylate diluted with 20 ml of methanol are then introduced dropwise, at the same temperature. The mixture is heated under reflux for about 2 hours. The insoluble material is removed by filtration and the methanol is evaporated. The residue is taken up in ether, the ether phase is washed with water and dried over magnesium sulphate, and the ether is evaporated. 14.8 g of oil are obtained; this oil, distilled under 0.1 mm Hg at a temperature of 135° C., gives 11.2 g of 4-(2-cyclobutylmethylthio-ethyl)-1-methoxy-benzene, which crystallises. M.p.=52° C. Yield: 72%.

Analysis: Calculated %: C 62.66; H 7.51; S 11.95. Found %: C 62.52; H 7.55; S 11.89; C 62.53; H 7.57; S 11.92.

10 g (0.042 mol) of the above compound and 7.3 g (0.063 mol) of pyridine hydrochloride are introduced into an Erlenmeyer flask which is placed under nitrogen and equipped with a reflux condenser. The mixture is immersed in an oil-bath at 210° C. This temperature is maintained, whilst stirring, for 45 minutes, the mixture is cooled and the solid mass is taken up with ether. Water is added. The mixture is decanted and the ether phase is washed repeatedly with water. The ether is dried over magnesium sulphate and evaporated. 7.8 g of an oil are obtained, which, after distillation at 145° C. under 0.5 mm Hg, gives 6.1 g of p-(2-cyclobutylmethylthio-ethyl)-phenol. Yield: 65%.

Analysis: Calculated %: C 70.22; H 8.16; S 14.42. Found %: C 70.05; H 8.22; S 14.51; C 70.13; H 8.35; S 14.45.

(1) 13 g (0.058 mol) of p-(2-cyclobutylmethylthio-ethyl)-phenol suspended in 80 ml of water are introduced into an Erlenmeyer flask placed under nitrogen. The temperature is kept below 20° C. and 2.72 g (0.068 mol) of sodium hydroxide pellets are added. The solution becomes homogeneous. It is stirred for about 30 minutes and 11.92 g (0.087 mol) of epibromohydrin are then added dropwise at ambient temperature. The batch is stirred at ambient temperature for about 4 hours. The solution becomes cloudy. The oily phase is extracted with ether and the ether phase is washed with 2 N sodium hydroxide solution and then with water. The ether is dried over magnesium sulphate and then evaporated. The residue is distilled on a bulb still at a temperature of 160° C. under a pressure of 0.04 mm Hg. 6.2 g (yield: 38.8%) of 1-[4-(2-cyclobutylmethylthio-ethyl)-phenoxy]-2,3-epoxy-propane are obtained, and this material is used directly.

(2) 6.2 g (0.0129 mol) of the preceding epoxide and 14 ml of isopropylamine are introduced into an Erlenmeyer flask placed under nitrogen. The mixture is stirred at ambient temperature for about 72 hours, the excess isopropylamine is evaporated, by entrainment with a little toluene. The solid product obtained is distilled at a temperature of 180° C. and under 0.04 mm Hg. 1.4 g (yield: 32%) of 1-[4-(2-cyclobutylmethylthio-ethyl)-phenoxy]-3-isopropylamino-propan-2-ol are obtained. M.p.=52° C.

Analysis: Calculated %: C 67.61; H 9.26; N 4.15; S 9.50. Found %: C 67.25; H 9.38; N 4.08; S 9.60; C 67.44; H 9.54; N 4.02; S 9.51.

The NMR spectrum is in agreement with the structure.

EXAMPLE XV

1-[4-(2-Cyclobutylmethylsulphonyl-ethyl)-phenoxy]-3-isopropylamino-propan-2-ol and its hydrochloride

[(I): p=3; q=1; m=2; n=0; R=CH(CH$_3$)$_2$; X=SO$_2$; code number: SLE-060]

Preparation of the starting compound:
4-(2-cyclobutylmethylsulphonyl-ethyl)-phenol.

20.6 g of 85% pure m-chloroperbenzoic acid and 100 ml of methylene chloride are introduced into a three-neck flask equipped with a magnetic stirrer. The mixture is cooled to $-10°$ C. and 12 g of 4-(2-cyclobutylmethylthioethyl)-1-methoxy-benzene are introduced dropwise, whilst ensuring that the temperature remains at $\leq -10°$ C.

After the end of the introduction, the mixture is kept for one hour at between $-10°$ C. and $0°$ C. It is allowed to return to ambient temperature, the precipitate is removed by filtration, the methylene chloride is evaporated and the solid residue is taken up in ether. The ether solution is washed with aqueous bicarbonate solution and then with water, and is dried over magnesium sulphate. The ether is evaporated and the solid residue is crystallised from a 90/10 mixture of methanol and water. 11 g of 4-(2-cyclobutylmethylsulphonyl-ethyl)-1-methoxybenzene are obtained.

Yield 80.9%. M.p.=52° C.

Analysis: Calculated %: C 62.66; H 7.51; S 11.95. Found %: C 62.52; H 7.55; S 11.89; C 62.53; H 7.57; S 11.92.

10 g of the preceding compound and 6.35 g of pyridine hydrochloride are introduced into an Erlenmeyer flask placed under nitrogen. The mixture is immersed in an oil-bath at 180°-190° C. and is kept at this temperature for one hour, whilst stirring. After cooling, water is added and the mixture is extracted with ether. The ether phase is washed with water, dried over magnesium sulphate and evaporated. 8.7 g of pure, solid 4-(2-cyclobutylmethylsulphonyl-ethyl)-phenol are obtained. Yield: 92.5%. M.p.=112° C.

(1) 8.6 g of 4-(2-cyclobutylmethylsulphonyl-ethyl)-phenol and 150 ml of water are introduced into an Erlenmeyer flask placed under nitrogen. The mixture is stirred in such a way that the solid is in suspension. 1.7 g of sodium hydroxide pellets are added whilst maintaining the temperature at 20° C. or below. All the material dissolves. 6.94 g of epibromohydrin are added dropwise at ambient temperature. The mixture is stirred overnight. The epoxide precipitates gradually. The mixture is cooled to 10° C. and the precipitate is filtered off. It is taken up in ether and the ether solution is washed with water and dried over magnesium sulphate. After evaporating the ether, 8.8 g of 1-[4-(2-cyclobutylmethylsulphonyl-ethyl)-phenoxy]-2,3-epoxy propane, which is used directly, are obtained:

(2) 8.6 g of the preceding epoxide and 80 ml of isopropylamine are stirred at ambient temperature for about 72 hours. The epoxide dissolves. The excess isopropylamine is evaporated. The solid residue is triturated with petroleum ether and then filtered off. After a pass over a silica column, and recrystallisation from isopropyl ether, 3 g of 1-[4-(2-cyclobutylmethylsulphonyl-ethyl)-phenoxy]-3-isopropylamino-propan-2-ol are obtained. M.p.=98° C.

Hydrochloride SLE-060:

The base is dissolved in the minimum amount of ethanol, the theoretical amount of a solution of hydrogen chloride in ether is added. The hydrochloride precipitates. It is recrystallised from a mixture of ethanol and ether. 2.7 g of pure hydrochloride are obtained. Yield: 27% M.p.=143° C.

Analysis: Calculated %: C 56.21; H 7.94; N 3.45; Cl 8.73; S 7.90. Found %: C 56.33; H 8.13; N 3.30; Cl 8.54; S 8.14; C 56.19; H 8.06; N 3.35; Cl 8.73; S 8.17.

EXAMPLE XVI

1-[4-(2-Cyclopropylmethylsulphonyl-ethoxy)-phenoxy]-3-isopropylamino-propan-2-ol

[(I); p=2; q=1; m=2; n=1; R=CH(CH$_3$)$_2$; X=SO$_2$; code number: SLE-155]

7 g (0.02 mol) of 1-[4-(2-cyclopropylmethylthioethoxy)-phenoxy]-3-isopropylamino-propan-2-ol are dissolved in 7 cm$^3$ of CH$_3$COOH. The solution is cooled to 0° C. and 5 cm$^3$ of H$_2$O$_2$ of 110 volumes strength are added dropwise. The mixture is allowed to return to ordinary temperature and is then heated for ¾ hour at 75°–80° C., and concentrated to dryness. The residue is taken up in MeOH. This solution is passed over an ion exchange column so as to give 1-[4-(2-cyclopropylmethylsulphonyl-ethoxy)-phenoxy]-3-isopropylamino-propan-2-ol.

After chromatography over a silica column, the base is crystallised from ether. After recrystallisation from isopropanol, the compound melts at 90°–92° C.

Weight obtained: 2 g. Yield: 27%.

Table I which follows lists all the compounds of the invention which have been prepared. The characteristics given are the melting points (in °C.) of the base or of a salt.

TABLE I

FORMULA I: (CH$_2$)$_p$–CH–(CH$_2$)$_q$–X–(CH$_2$)$_m$–(O)$_n$–C$_6$H$_4$–O–CH$_2$–CHOH–CH$_2$–NH–R

| Code No. | Ex. | p | q | m | n | R | X | Characteristics (M.p. in °C.) | |
|---|---|---|---|---|---|---|---|---|---|
| SLD-177 | 1 | 2 | 1 | 2 | 1 | CH(CH$_3$)$_2$ | 0 | Hydrochloride | 94–6 |
| SLD-178 | 2 | 2 | 1 | 2 | 1 | C(CH$_3$)$_3$ | 0 | Neutral fumarate | 158–60 |
| SLD-212 | 3 | 2 | 1 | 2 | 0 | CH(CH$_3$)$_2$ | 0 | Hydrochloride base 71 | 116 |
| SLD-224 | 4 | 2 | 1 | 1 | 0 | CH(CH$_3$)$_2$ | 0 | base 48 | |
| SLD-230 | 5 | 2 | 1 | 0 | 0 | CH(CH$_3$)$_2$ | 0 | Hydrochloride base 78–80 | 144 |
| SLD-231 | 6 | 2 | 1 | 0 | 0 | C(CH$_3$)$_3$ | 0 | Hydrochloride base 90–2 | 146–7 |
| SLD-254 | 7 | 3 | 1 | 2 | 0 | CH(CH$_3$)$_2$ | 0 | base 63 | |
| SLE-020 | | | | | | | | hydrochloride | 104 |
| | | | | | | | | acid fumarate | 157 |
| SLD-268 | 8 | 5 | 1 | 2 | 0 | CH(CH$_3$)$_2$ | 0 | Hydrochloride | 122 |
| SLD-311 | 9 | 2 | 3 | 0 | 0 | CH(CH$_3$)$_2$ | 0 | Hydrochloride | 115 |
| SLE-096 | 10 | 3 | 1 | 2 | 1 | CH(CH$_3$)$_2$ | 0 | Hydrochloride base 56 | 97 |
| SLE-024 | 11 | 3 | 1 | 2 | 0 | CH(CH$_2$CN)(CH$_3$) | 0 | Hydrochloride | 126 |
| SLE-204 | 27 | 3 | 1 | 2 | 1 | (CH$_2$)$_2$–C$_6$H$_3$(OCH$_3$)$_2$ | 0 | Base 79–80 Hydrochloride | 146 |
| SLE-025 | 12 | 3 | 1 | 2 | 0 | (CH$_2$)$_2$NHCOCH$_3$ | 0 | Hydrochloride | 150 |
| SLD-299 | 13 | 2 | 1 | 2 | 1 | CH(CH$_3$)$_2$ | S | Hydrochloride | 86 |
| SLE-056 | 14 | 3 | 1 | 2 | 0 | CH(CH$_3$)$_2$ | S | Base 52 | |
| SLE-060 | 15 | 3 | 1 | 2 | 0 | CH(CH$_3$)$_2$ | SO$_2$ | Hydrochloride base 98 | 143 |
| SLE-155 | 16 | 2 | 1 | 2 | 1 | CH(CH$_3$)$_2$ | SO$_2$ | Base 91 | |
| SLD-291 | 17 | 4 | 1 | 2 | 0 | CH(CH$_3$)$_2$ | 0 | Neutral fumarate | 139 |
| SLE-080 | 18 | 3 | 1 | 1 | 0 | CH(CH$_3$)$_2$ | 0 | Hydrochloride base 58 | 98 |
| SLE-185 | 25 | 3 | 1 | 2 | 1 | CH(CH$_3$)$_2$ | S | Hydrochloride | 91 |
| SLE-203 | 26 | 4 | 1 | 2 | 1 | CH(CH$_3$)$_2$ | 0 | Base 65 Hydrochloride | 101–102 |
| SLE-049 | 19 | 3 | 1 | 2 | 0 | –CH(CH$_3$)–(CH$_2$)$_2$–C$_6$H$_5$ | 0 | Base 56 | |
| SLE-055 | 20 | 3 | 1 | 2 | 0 | –CH(CH$_3$)–(CH$_2$)$_2$–C$_6$H$_4$–OCH$_3$ | 0 | Base 57 | |
| SLE-059 | 21 | 3 | 1 | 2 | 0 | –CH(CH$_3$)–(CH$_2$)$_2$–C$_6$H$_4$–F | 0 | Base 56 | |

TABLE I-continued

FORMULA I: $(CH_2)_p$ $CH-(CH_2)_q-X-(CH_2)_m-(O)_n$—⟨⟩—$O-CH_2-CHOH-CH_2-NH-R$

| Code No. | Ex. | p | q | m | n | R | X | Characteristics (M.p. in °C.) | |
|---|---|---|---|---|---|---|---|---|---|
| SLE-111 | 22 | 3 | 1 | 2 | 0 | $-(CH_2)_2-$⟨⟩$-OCH_3$, $OCH_3$ | 0 | Hydrochloride base 54 | 152 |
| SLE-150 | 23 | 3 | 1 | 2 | 0 | ▷ | 0 | Hydrochloride | 130 |
| SLE-061 | 24 | 3 | 1 | 3 | 0 | $CH(CH_3)_2$ | 0 | Acid oxalate | 117 |

The compounds (I) of the invention were subjected to a series of pharmacological tests which demonstrated their valuable properties in the cardio-vascular field. Their selective β-blocking properties were investigated and studied in comparison with those of metoprolol or 1-[4-(2-methoxy-ethyl)-phenoxy]-3-isopropylamino-propan-2-ol, which is itself a selective blocking agent of β-adrenergic receptors.

METHODS

Acute toxicity:

The acute toxicity for oral and intravenous administration was evaluated for CD1 male mice of average weight 20 g. The mortality was recorded over a period of 5 days following the administration of the compounds. The 50% lethal dose (LD 50) was calculated according to Litchfield and Wilcoxon (J. Pharmacol. Exp. Ther 1944, 95, 99).

The results are summarized in Table II.

Studies on isolated organs:

Isolated auricles taken from rats weighing 250 to 350 g and kept in Moran solution (in g/l: NaCl=7.02; KCl=0.42; $CaCl_2$=0.24; $MgCl_2$=0.20; $NaHCO_3$=2.0; glucose=1.8), oxygenated (95% $O_2$-5% $CO_2$) at a temperature of 31° C., were used. The tachycardia and the increase in the contractile force, brought about by isoprenaline were studied (from the curve of the dose against the response to the agonist) before and after the addition of the antagonist (compounds (I) or reference substance), and the $pA_2$ for each was calculated by the method of Arunlakshana and Schild (Brit. J. Pharmacol. 1959, 14, 48); the $pA_2$ represents the logarithm of the molar concentration of competitive antagonist which requires twice as strong a dose of agonist in order to bring about the same responses as those obtained in the absence of the antagonist. The $pA_2$ found are listed in Table III.

TABLE II

| | LD50 mg . $kg^{-1}$ (confidence limits: 95%) | |
|---|---|---|
| | MOUSE | |
| COMPOUND | ORAL ADMINISTRATION | INTRAVENOUS ADMINISTRATION |
| METOPROLOL | 1050 (766–1438) | 62 (56–68) |
| SL D.177 | 610 (550–665) | 76 (72–79) |
| SL D.178 | 445 (380–520) | 53 (46–61) |
| SL D.212 | 944 (656–1359) | 37 (32–44) |
| SL D.224 | 1400 (1238–1582) | 88 (64–121) |
| SL D.230 | 750 (385–1462) | 43 (31–48) |
| SL D.231 | 1200 (800–1800) | 36 (30–41) |
| SL D.254 | 658 (562–770) | 28 (26–31) |
| SL E.020 | | |
| SL D.268 | | 35 (30–42) |
| SL D.291 | | 56 (48–64) |
| SL D.311 | | 71 (55–92) |

TABLE III

| | | EFFECT ON CHRONOTROPISM | | EFFECT ON INOTROPISM | |
|---|---|---|---|---|---|
| COMPOUND | EX. | $pA_2$ | RATIO OF ACTIVITY TO THAT OF METOPROLOL | $pA_2$ | RATIO OF ACTIVITY TO THAT OF METOPROLOL |
| METOPROLOL | — | 7.64 | 1.0 | 7.94 | 1.0 |
| SL D.177 | 1 | 8.09 | 2.8 | 7.97 | 1.1 |
| SL D.178 | 2 | 7.70 | 1.4 | 7.96 | 1.0 |
| SL D.212 | 3 | 8.53 | 7.8 | 8.29 | 2.2 |
| SL D.224 | 4 | 8.01 | 2.3 | 7.89 | 0.9 |
| SL D.230 | 5 | 8.30 | 4.6 | 8.27 | 2.1 |
| SL D.231 | 6 | 7.54 | 0.8 | 7.47 | 0.3 |
| SL D.254 SL E.020 | 7 | 9.56 | 83.2 | 8.11 | 1.5 |
| SL D.268 | 8 | 6.84 | 0.2 | 6.40 | 0.03 |
| SL D.311 | 9 | 7.04 | 0.2 | 7.28 | 0.2 |
| SL E.203 | 26 | 8.26 | 4.17 | 7.97 | 1.00 |
| SL E.096 | 10 | 8.25 | 4.1 | 8.29 | 2.2 |
| SL E.024 | 11 | 6.47 | 0.07 | 6.21 | 0.02 |
| SL E.025 | 12 | 7.43 | 0.6 | 7.21 | 0.2 |
| SL D.299 | 13 | 7.76 | 1.3 | 7.83 | 0.8 |
| SL D.056 | 14 | 7.11 | 0.3 | 6.88 | 0.09 |
| SL E.060 | 15 | 7.93 | 1.9 | 7.94 | 1.0 |
| SL E.155 | 16 | 6.79 | 0.1 | 6.85 | 0.08 |
| SL D.291 | 17 | 6.89 | 0.2 | 6.83 | 0.08 |
| SL E.080 | 18 | 7.44 | 0.6 | 7.52 | 0.4 |
| SL E.049 | 19 | 5.11 | — | 5.91 | 0.01 |
| SL E.059 | 21 | 5.54 | — | 6.16 | 0.02 |
| SL E.111 | 22 | 7.75 | 1.3 | 7.13 | 0.1 |

TABLE III-continued

| COMPOUND | EX. | EFFECT ON CHRONOTROPISM | | EFFECT ON INOTROPISM | |
|---|---|---|---|---|---|
| | | pA₂ | RATIO OF ACTIVITY TO THAT OF METOPROLOL | pA₂ | RATIO OF ACTIVITY TO THAT OF METOPROLOL |
| SE E.061 | 24 | 7.02 | 0.2 | 7.05 | 0.1 |

All the compounds (I) possess an inhibiting activity in respect of the cardiac effects of isoprenaline but not in respect of the hypotensive effects of this compound; they are thus indeed selective blocking agents of the $\beta_1$-adrenergic receptors, that is to say of the $\beta$-adrenergic receptors located at the heart, but not of the $\beta_2$-adrenergic receptors, located at the vessels.

Finally, the compounds of the invention are noteworthy for their therapeutic index, which is much more favourable than that of metoprolol.

The compounds which have proved to be particularly valuable are the compounds SL D.212, SL E.020, SL E.096 and SL D.299.

The preceding results show that the compounds of the invention can be used in human and veterinary medicine, in cardio-vascular illnesses and especially in coronary conditions, conditions affecting the myocardium and disturbances of the heart beat.

The invention consequently comprises pharmaceutical compositions which contain the compounds of the general formula (I) and their salts as active principles in association with excipients suitable for their oral, rectal or parenteral administration. These pharmaceutical compositions can also contain other medicamentous substances with which these compounds and their salts are pharmaceutically and therapeutically compatible.

For oral administration, all the pharmaceutical forms suitable for this methods of administration are used, that is to say tablets, dragees, pills capsules, cachets and potable solutions and suspensions; the unit dose of the active principle can vary between 20 and 100 mg and the daily dose is between 40 and 800 mg.

For endorectal administration, suppositories containing 40 to 300 mg of active principle, and administered to the patient at the rate of 1 to 3 per 24 hours, are used.

For parenteral administration, stabilised and buffered injectable solutions prepared beforehand or at the time of use are employed. The dose of active principle per unit dose can vary between 5 and 50 mg and the daily dose is between 5 and 300 mg.

We claim:

1. A compound of the formula

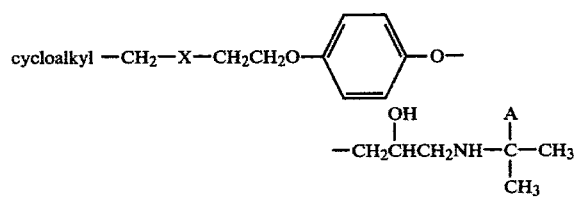

wherein
cycloalkyl is cyclopropyl, cyclobutyl, cycloamyl or cyclohexyl;
X is —O—, —S— or —SO₂—; and
A is hydrogen or methyl; or a pharmaceutically acceptable salt thereof.

2. A compound of claim 1 wherein said cycloalkyl is cyclopropyl.
3. A compound of claim 1 wherein X is —O—.
4. A compound of claim 1 wherein X is —S—.
5. A compound of claim 1 wherein X is —SO₂—.
6. A compound of claim 2 wherein X is —O—.
7. The compound of claim 5 which is 1-[4-(2-cyclopropylmethylsulfonylethoxy)-phenoxy]-3-isopropylaminopropan-2-ol or a pharmaceutically acceptable salt thereof.
8. A compound of claim 6 which is 1-[4-(2-cyclobutylmethoxy-ethoxy)-phenoxy]-3-isopropylamino-propan-2-ol or a pharmaceutically acceptable salt thereof.
9. A compound of claim 4 which is 1-[4-(2-cyclopropylmethylthio-ethoxy)-phenoxy]-3-isopropylaminopropan-2-ol or a pharmaceutically acceptable salt thereof.
10. A compound of claim 6 which is 1-[4-(2-cyclopropylmethoxy-ethoxy)-phenoxy]-3-isopropylaminopropan-2-ol or a pharmaceutically acceptable salt thereof.
11. A compound of claim 6 which is 1-[4-(2-cyclopropylmethoxy-ethoxy)-phenoxy]-3-t-butylamino-propan-2-ol or a pharmaceutically acceptable salt thereof.
12. A compound of the formula

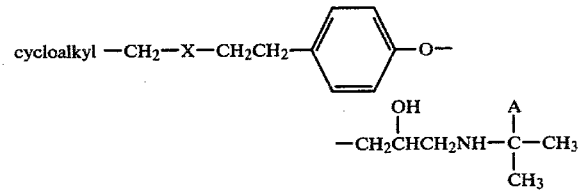

wherein
cycloalkyl is cyclopropyl, cyclobutyl, cycloamyl or cyclohexyl;
X is —O—, —S— or —SO₂—; and
A is hydrogen or methyl
or a pharmaceutically acceptable salt thereof.
13. A compound of claim 12 which is 1-[4-(2-cyclobutylmethylsulfonyl-ethyl)-phenoxy]-3-isopropylamino-propan-2-ol or a pharmaceutically acceptable salt thereof.
14. A compound of claim 12 which is 1-[4-(2-cyclobutylmethoxy-ethyl)-phenoxy]-3-isopropylaminopropan-2-ol or a pharmaceutically acceptable salt thereof.
15. The compound of claim 12 which is 1-[4-(2-cyclobutylmethylthio-ethyl)-phenoxy]-3-isopropylaminopropan-2-ol or a pharmaceutically acceptable salt thereof.
16. A method for the selective blocking of $\beta_1$-adrenergic receptors which comprises introducing into the environment of said receptors an effective amount of 1-[4-(2-cyclopropylmethoxy-ethyl)-phenoxy]-3-isopropylamino-propan-2-ol whereby said $\beta_1$-andrenergic receptors are blocked.

17. A method for the selective blocking of $\beta_1$-adrenergic receptors which comprises introducing into the environment of said receptors an effective amount of a compound of claim 1, 8, 9, 10, 11, or 7, whereby said $\beta_1$-adrenergic receptors are blocked.

18. A method for the selective blocking of $\beta_1$-adrenergic receptors which comprises introducing into the environment of said receptors an effective amount of a compound of claim 12, 13, 14, or 15, whereby said $\beta_1$-adrenergic receptors are blocked.

* * * * *

UNITED STATES PATENT AND TRADEMARK OFFICE
CERTIFICATE OF CORRECTION

PATENT NO. : 4,311,708

DATED : January 19, 1982

INVENTOR(S) : PHILIPPE MJ MANOURY ET AL

It is certified that error appears in the above—identified patent and that said Letters Patent is hereby corrected as shown below:

Column 2, lines 66-67, in the formula, please change to

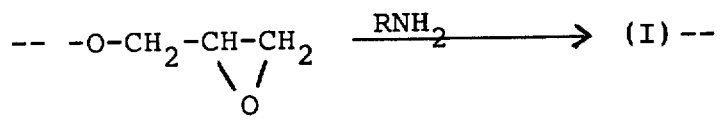

Column 3, line 54, in the formula, delete the dash between "$(CH_2)_p$" and "CH"

Column 5, line 9, change "cf" to --of--

Column 6, line 48, in the formula, change the first "2" to --1--

UNITED STATES PATENT AND TRADEMARK OFFICE
CERTIFICATE OF CORRECTION

PATENT NO. : 4,311,708

DATED : January 19, 1982

INVENTOR(S) : PHILIPPE MJ MANOURY ET AL

It is certified that error appears in the above—identified patent and that said Letters Patent is hereby corrected as shown below:

Column 19, Table III, change "Metroprolol" to

--Metoprolol-- and change " { " to -- } --

Signed and Sealed this

First Day of June 1982

[SEAL]

Attest:

Attesting Officer

GERALD J. MOSSINGHOFF

Commissioner of Patents and Trademarks